Figure 1:
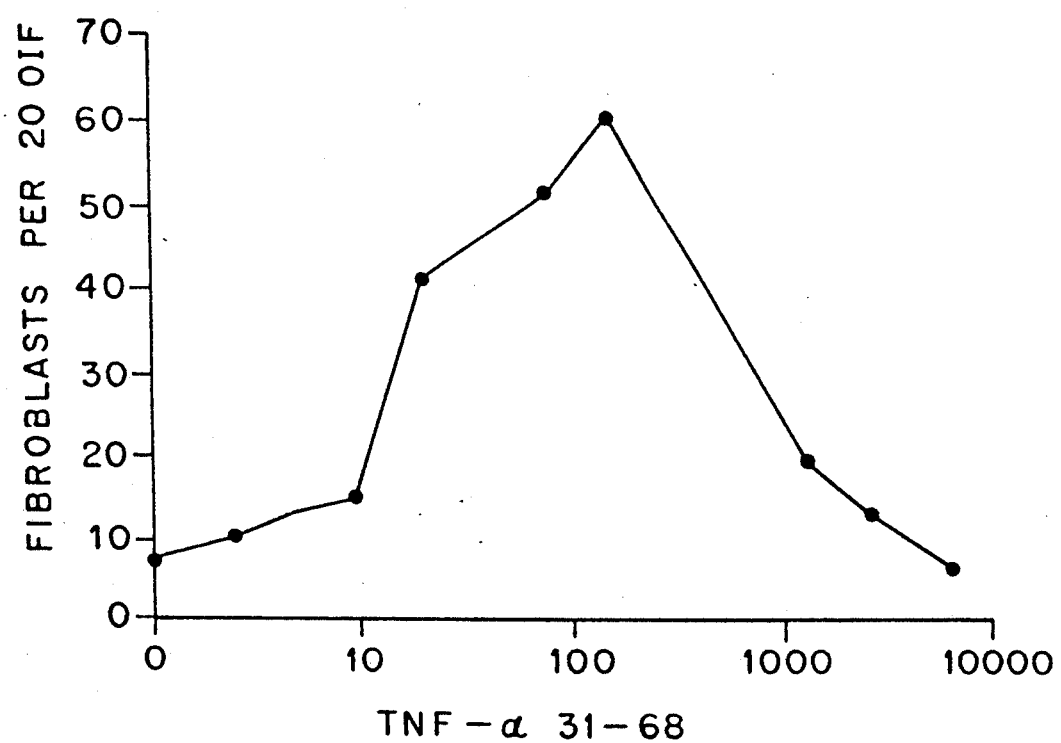

United States Patent [19]

Postlethwaite et al.

[11] Patent Number: 5,160,483
[45] Date of Patent: Nov. 3, 1992

[54] FRAGMENT OF TNF-α FOR PROMOTING WOUND HEALING

[75] Inventors: Arnold E. Postlethwaite, Eads; Jerome M. Seyer; Andrew H. Kang, both of Memphis, all of Tenn.

[73] Assignee: The University of Tennessee Research Corporation, Knoxville, Tenn.

[21] Appl. No.: 697,642

[22] Filed: May 7, 1991

[51] Int. Cl.$^5$ ............................ A61K 37/00; A61K 45/05
[52] U.S. Cl. ............................................ 424/85.1; 514/12
[58] Field of Search ........................... 514/12; 424/85.1

[56] References Cited

U.S. PATENT DOCUMENTS

| | | | |
|---|---|---|---|
| 4,650,674 | 3/1987 | Aggarwal et al. | 424/85 |
| 4,677,063 | 6/1987 | Mark et al. | 435/68 |
| 4,732,972 | 3/1988 | Felix et al. | 530/324 |
| 4,806,492 | 2/1989 | Soyab et al. | 436/547 |
| 4,808,402 | 2/1989 | Leibovich et al. | 424/423 |
| 4,816,561 | 3/1989 | Todaro | 530/324 |
| 4,845,075 | 7/1989 | Murray et al. | 514/12 |
| 4,857,314 | 8/1989 | O'Connor et al. | 424/85 |
| 4,861,757 | 8/1989 | Antoniades et al. | 514/23 |
| 4,894,439 | 1/1990 | Gorin et al. | 530/351 |
| 4,929,442 | 5/1990 | Powell | 424/85 |
| 4,957,742 | 9/1990 | Knighton | 424/532 |

OTHER PUBLICATIONS

Abstract—Human Recombinant Tumor Necrosis Factor Alpha Is a Fibroblast Chemoattractant—Arnold E. Postlethwaite—Clinical Research vol. 38, No. 2, 1990, 478A.

Stimulation of Fibroblast Chemotaxis by Human Recombinant Tumor Necrosis Factor Alpha (TNF-Alpha) and a Synthetic TNF-Alpha 31-68 Peptide Arnold E. Postlethwaite and Jerome M. Seyer The Journal of Experimental Medicine—vol. 172—Dec., 1990, 1749-1756.

Primary Examiner—Merrell C. Cashion, Jr.
Assistant Examiner—Choon P. Koh
Attorney, Agent, or Firm—Luedeka, Hodges, Neely & Graham

[57] ABSTRACT

A method and composition for promoting the healing of an open wound, such as a fresh surgical incision, a decubitus ulcer, or a diabetes ulcer. The method includes applying to the wound a therapeutically effective amount of a composition comprising a protein fragment of tumor necrosis factor α(TNF-α) including amino acids 31 through 68 SEQ ID NO.: 1. The composition may be applied topically or injected locally into a wound or ulcer site. A preferred composition includes a carrier medium selected from sterile water, sterile saline, and albumin. Topical formulations are administered as sprays, gels, ointments or salves.

10 Claims, 1 Drawing Sheet

FRAGMENT OF TNF-α FOR PROMOTING WOUND HEALING

Work on this invention was supported by funds from the Veterans Administration Medical Center, Memphis, Tennessee, and by grants from the National Institutes of Health. The U.S. government has certain rights in this invention.

The present invention relates generally to compositions for promoting the healing of wounds, particularly open wounds (e.g.. diabetic ulcers, decubitus ulcers or burns), and to methods for treating such wounds. The present invention also relates to compositions comprising protein fragments for the treatment of open wounds.

Macrophages are a major source of fibrogenic factors that promote the healing of open wounds, such as fresh surgical incisions, burns, decubitus ulcers, and diabetes ulcers. Such damaged connective tissue results in various types of trauma, inflammation, and immune reactions. An early event in fibrogenesis is the recruitment of neighboring fibroblasts to the site of injury to synthesize and remodel a new connective tissue mixture. Several macrophage-derived fibroblast chemoattractants (e.g., transforming factor β[TGF-B], fibronectin, platelet-derived growth factor [PDGF], and tumor necrosis factor α[TNF-α]) have been previously described that direct this fibroblast recruitment. These chemoattractants show strong chemotaxis, that is, the ability to induce the migration of cells to a specific site. The application of these materials to the site of an open wound results in a measurable increase in the number of fibroblasts and monocytes migrating to the area of the wound. This, in turn, results in a decreased healing time for the wound.

The widespread use of the previous chemoattractants has been severely hampered by several important difficulties. Since the compounds are derived from living cells, their production and recovery is relatively expensive and time consuming. It is difficult to separate pure materials from the melange of other chemicals that are produced by living cells and much of the material is lost in the separation process. In addition, the materials are so large and complicated that their production by recombinant techniques or automated synthesis is prohibitively time consuming and expensive.

Another problem is that the chemoattractant materials previously described have relatively large molecular weights (e.g., greater than 17,000 Da) and are not readily absorbed into the wound site. Therefore, many more doses (and larger doses) of the material are needed for treatment than would be indicated by the size and severity of a particular wound.

An additional problem curtailing the use of presently available materials is the sensitivity shown by some patients to materials derived from living cells. This reactivity, a result of impurities in the preparation or the reactions of patients to certain portions of the materials, severely limits the amounts of material that can be safely used with patients. In some cases, the amount of material that certain patients can tolerate may fall below the effective limits of the material required to induce fibroblast migration. Also, at least one of the currently available proteins, TNF-α, is known to be a cytotoxin as well as a chemoattractant. The cytotoxioity of the protein further limits the number and size of the doses of TNF-α that may be applied to a wound without cell damage.

As a result of these and other problems, the use of previously developed chemoattractants has been severely restricted to experimentation and very limited commercial applications. Therefore, there is a need for a chemoattractant that is relatively inexpensive, simple to prepare, easy to apply to the wound, and of such size to be readily absorbed in the area of the wound, not subject to patient sensitivity and noncytotoxic.

Accordingly, it is an object of the present invention to provide a material for treating and promoting the healing of wounds that is relatively inexpensive and easy to prepare.

It is a further object of the invention to provide such material that is easy to apply to the area of the wound and is small enough to be readily absorbed at the site of the wound.

It is another object of the invention to provide a material that neither induces a sensitivity reaction nor has the cytotoxicity of the previously used materials.

It has been unexpectedly discovered that the intradermal injection of a composition which includes a polypeptide fragment of tumor necrosis factor α (TNF-α) in guinea pigs results in an increased migration of fibroblasts and monocytes into the area of the wound. There is also an increase in the amount of connective tissue at the injection site. The composition accomplishes this without the problems attendant on the previously developed materials. The fragment includes amino acids 31 through 68 SEQ ID No.: 1 of TNF-α which has the sequence:

```
31                    35                      40                        45
Arg—Arg—Ala—Asn—Ala—Leu—Leu—Ala—Asn—Gly—Val—Glu—Leu—Arg—Asp—

50                      55                        60
Asn—Gln—Leu—Val—Val—Pro—Ser—Glu—Gly—Leu—Tyr—Leu—Ile—Tyr—Ser—

65                      68
Gln—Val—Leu—Phe—Lys—Gly—Gln—Gly.
```

In a preferred composition, the fragment is compounded with sterile water, sterile saline or albumin to form the composition as a spray, gel, ointment or salve that is applied to the wound. The dosage used will be influenced by the type of wound and the nature of the cell proliferation activity in the wound.

Surprisingly, the relatively small size of the fragment, when compared to the complete proteins heretofore used, avoids the problems encountered with the previous preparations. The cells at the site of the injury readily absorb and retain the fragment of the present invention. Fibroblasts and monocytes are thereby continually attracted to the site of the wound long after other chemoattractants disappear from the area of the injury. Therefore, a composition containing the fragment does not need to be applied as often as the materials previously developed. Since much less material needs to be applied to the wound, there will be less sensitivity to the application of the fragment than to the application of the previously used materials.

Unexpectedly, the composition of the present invention induces the chemotaxis of fibroblasts and monocytes, like the complete, unfragmented TNF-α, but without any showing of cytotoxicity, quite unlike TNF-α. This complete lack of cytotoxicity means that much more of the fragment can be applied to the wound to aid in healing without risking the cell damage that might occur with the use of the complete protein.

Thus, the present invention provides a composition that promotes the healing of open wounds without the problems associated with compositions previously developed.

FIG. 1 is a graphical representation of the ability of the composition of the present invention to induce the migration of fibroblasts. The FIGURE shows that fibroblasts are induced to migrate in the presence of the protein fragment of the composition.

The polypeptide fragment of the present invention is synthesized by a solid-phase method that is well known in the art (R. B. Merrifield, "Solid Phase Synthesis I. The Synthesis of a Tetrapeptide", *J. Am. Chem. Soc.*, vol. 85, p. 2149, 1963) with the aid of an automated peptide synthesizer. The fragment is further purified by gel filtration and reverse-phase high performance liquid chromatography (RP HPLC). The composition of the fragment is confirmed by an automatic amino acid analyzer. This common technique allows the automatic, rapid and inexpensive production of the fragment.

For topical application to wounds, burns or decubitus or other skin ulcerations, the peptide is formulated in amounts sufficient to induce soft tissue repair with pharmaceutically acceptable carriers that are added for the particular mode of administration. Topical dosage forms include sprays, gels, ointments, or salves.

In order to provide a more complete understanding of the invention, the following Example is given by way of illustration and not by way of limitation.

EXAMPLE I

Chemotaxis of Fibroblasts to TNF-α, Amino Acid Fragment 31-68 SEQ ID No.: 1

Solutions of varying concentrations of the fragment of TNF-α comprising amino acids 31 through 68 SEQ ID No.: 1 in phosphate buffered saline (PBS) were added to the lower compartment of chemotaxis chambers. The number of fibroblasts migrating to the lower compartment was counted. The results are shown in FIG. 1. The response curve is bell-shaped, with a maximum at 100 nM. An analysis of the effects of varying concentration gradients of the protein fragment (a Zigmond-Hirsch checkerboard analysis) was performed by adding different concentrations of the fragment to the upper and/or lower compartments of a chemotaxis chamber. The number of fibroblasts migrating to the lower surface of each filter was counted. The results of the analysis, shown in Table I, indicated that the fragment induced mostly chemotactic migration of fibroblasts.

TABLE I

| Fragment Concentration in Upper Compartment | Fragment Concentration in Lower Compartment | | | | |
|---|---|---|---|---|---|
| | 329 nM | 164 nM | 41 nM | 21 nM | 0 nM |
| 329 nM | 8 ± 1 | 12 ± 2 | 9 ± 1 | 10 ± 1 | 16 ± 3 |
| 164 nM | 43 ± 3 | 22 ± 4 | 16 ± 3 | 11 ± 1 | 14 ± 2 |
| 41 nM | 57 ± 6 | 47 ± 5 | 26 ± 4 | 28 ± 5 | 31 ± 2 |
| 21 nM | 67 ± 2 | 46 ± 2 | 49 ± 7 | 9 ± 1 | 20 ± 6 |

TABLE I-continued

| Fragment Concentration in Upper Compartment | Fragment Concentration in Lower Compartment | | | | |
|---|---|---|---|---|---|
| | 329 nM | 164 nM | 41 nM | 21 nM | 0 nM |
| 0 nM | 86 ± 13 | 73 ± 4 | 57 ± 3 | 31 ± 4 | 17 ± 3 |

The fibroblasts migrate from the upper chamber to the lower chamber since there is very little of the fragment in the upper chamber and there is quite a large concentration of the fragment in the lower chamber. This simulates the condition at a wound site where there has been an application of the fragment to the wound. The concentration of the fragment in the surrounding tissue will be quite low compared to the concentration at the wound site. Therefore, the fibroblasts will migrate from the area of low concentration of the fragment to the area of high concentration.

The relatively small molecular size (about 3,800 Da) of the peptide is a distinct advantage for the local absorbance through tissues at the sites of wounds. When compared to compounds (such as whole TNF-α, 17,000 Da), the peptide of this invention readily diffuses into fibroblasts and other cells. It is believed that this peptide then interacts with the intercellular molecules to promote wound healing.

Therefore, the present invention provides a composition for treating and promoting the healing of wounds that is relatively inexpensive and easy to prepare for use. Further, the invention provides such composition that is easy to apply to the area of the wound and is retained at the site of the wound while continuing to promote wound healing. Also, the invention provides a composition that does not induce the sensitivity or have the cytotoxicity of the previously developed materials.

Various of the features of the invention which are believed to be new are set forth in the appended claims.

(1) GENERAL INFORMATION:
  (i) APPLICANT: Postlethwaite, Arnold E.;
    Seyer, Jerome M.;
    Kang, Andrew H.
  (ii) TITLE OF INVENTION: FRAGMENT OF TNF-α FOR PROMOTING WOUND HEALING
  (iii) NUMBER OF SEQUENCES: 1
  (iv) CORRESPONDENCE ADDRESS:
    (A) ADDRESSEE: Luedeka, Hodges, Neely & Graham, P.C.
    (B) STREET: 1030 First American Center
    (C) CITY: Knoxville
    (D) STATE: Tennessee
    (E) COUNTRY: U.S.A.
    (F) ZIP 37902
  (v) COMPUTER READABLE FORM:
    (A) MEDIUM TYPE: Diskette, 5.25 inch, 360 Kb storage
    (B) COMPUTER: IBM XT
    (C) OPERATING SYSTEM: DOS 4.01
    (D) SOFTWARE: Word Perfect 5.0.1
  (vi) CURRENT APPLICATION DATA:
    (A) APPLICATION NUMBER: 07/697,642
    (B) FILING DATE: 07 May 1991
    (C) CLASSIFICATION: 514
  (viii) ATTORNEY/AGENT INFORMATION:
    (A) NAME: Paul E. Hodges
    (B) REGISTRATION NUMBER: 20,972
    (C) REFERENCE/DOCKET NUMBER: 47036.00
  (ix) TELECOMMUNICATIONS INFORMATION:
    (A) TELEPHONE: (615) 546-4305
    (B) TELEFAX: (615) 523-4478

-continued (2) INFORMATION FOR ID SEQ NO:1:
    (i) SEQUENCE CHARACTERISTICS:
        (A) LENGTH: 38 amino acid residues
        (B) TYPE: Amino Acid
        (D) TOPOLOGY: Linear
    (ii) MOLECULE TYPE: peptide
    (iii) HYPOTHETICAL: no
    (v) FRAGMENT TYPE: internal fragment
    (xi) SEQUENCE DESCRIPTION: SEQ ID NO:1

| Arg 31 | Arg | Ala | Asn | Ala 35 | Leu | Leu | Ala | Asn | Gly 40 |
|---|---|---|---|---|---|---|---|---|---|
| Val | Glu | Leu | Arg | Asp 45 | Asn | Gln | Leu | Val | Val 50 |
| Pro | Ser | Glu | Gly | Leu 50 | Tyr | Leu | Ile | Tyr | Ser 60 |
| Gln | Val | Leu | Phe | Lys 65 | Gly | Gln | Gly 68 | | |

What is claimed is:

1. A method for promoting the healing of a wound comprising applying to the wound a therapeutically effective dose of a composition consisting essentially of a protein fragment of tumor necrosis factor α (TNF-α) amino acids 31 through 68 SEQ ID No: 1.

2. The method of claim 1 wherein the composition is applied topically by direct contact with the wound.

3. The method of claim 2 wherein the wound is a fresh surgical incision.

4. The method of claim 2 wherein the wound is a decubitus ulcer.

5. The method of claim 2 wherein the wound is a diabetic ulcer.

6. The method of claim 1 wherein the composition further comprises a carrier medium selected from the group consisting of sterile water, sterile saline, and albumin.

7. The method of claim 1 including an initial step of preparing and purifying the protein fragment of TNF-α by recombinant nucleic acid techniques.

8. A composition for promoting the healing of wounds, the composition comprising:
    a protein fragment of TNF-α including amino acids 31 through 68 SEQ ID No.:1; and
    a carrier medium.

9. The composition of claim 8 wherein the protein fragment of TNF-α has the sequence SEQ ID No:1

31                         35                           40                         45
Arg—Arg—Ala—Asn—Ala—Leu—Leu—Ala—Asn—Gly—Val—Glu—Leu—Arg—Asp—

50                         55                         60
Asn—Gln—Leu—Val—Val—Pro—Ser—Glu—Gly—Leu—Tyr—Leu—Ile—Tyr—Ser—

65                         68
Gln—Val—Leu—Phe—Lys—Gly—Gln—Gly.

10. The composition of claim 8 wherein the carrier medium is selected from the group consisting of sterile water, sterile saline, and albumin.

* * * * *

UNITED STATES PATENT AND TRADEMARK OFFICE
CERTIFICATE OF CORRECTION

PATENT NO. : 5,160,483

DATED : November 3, 1992

INVENTOR(S) : Arnold E. Postlethwaite, Jerome M. Seyer and Andrew H. Kang

It is certified that error appears in the above-identified patent and that said Letters Patent is hereby corrected as shown below:

<u>Column 1 line 12</u>

After "e.g. insert --,--.

<u>Column 2, line 5</u>

Delete "cytotoxioity" and insert --cytotoxicity-- therefor.

<u>Column 4, line 46</u>

Delete "TNF-αFOR" and insert --TNF-α FOR-- therefor.

Signed and Sealed this

Twenty-sixth Day of October, 1993

Attest:

BRUCE LEHMAN

Attesting Officer     Commissioner of Patents and Trademarks